(12) United States Patent
Jain et al.

(10) Patent No.: US 9,078,830 B2
(45) Date of Patent: Jul. 14, 2015

(54) MULTI-LAYERED, MULTIPLE UNIT PHARMACEUTICAL COMPOSITIONS

(75) Inventors: Paras Jain, Amravati (IN); Umesh Vinayakrao Barabde, Amravati (IN); Kanwarpreet Singh Bakshi, Gurgaon (IN); Rajan Kumar Verma, New Delhi (IN); Romi Barat Singh, Varanasi (IN)

(73) Assignee: RANBAXY LABORATORIES LIMITED, New Delhi (IN)

( * ) Notice: Subject to any disclaimer, the term of this patent is extended or adjusted under 35 U.S.C. 154(b) by 49 days.

(21) Appl. No.: 13/388,076

(22) PCT Filed: Jul. 28, 2010

(86) PCT No.: PCT/IB2010/053439
§ 371 (c)(1),
(2), (4) Date: Jul. 17, 2012

(87) PCT Pub. No.: WO2011/013082
PCT Pub. Date: Feb. 3, 2011

(65) Prior Publication Data
US 2012/0288532 A1    Nov. 15, 2012

(30) Foreign Application Priority Data
Jul. 31, 2009  (IN) .......................... 1587/DEL/2009

(51) Int. Cl.
*A61K 31/205* (2006.01)
*A61K 9/50* (2006.01)
*A61K 31/137* (2006.01)

(52) U.S. Cl.
CPC ............ *A61K 9/5078* (2013.01); *A61K 9/5047* (2013.01); *A61K 31/137* (2013.01)

(58) Field of Classification Search
USPC .......................................... 514/554
See application file for complete search history.

(56) References Cited

U.S. PATENT DOCUMENTS

| 4,927,640 | A | 5/1990 | Dahlinder et al. | 424/497 |
| 5,229,135 | A | 7/1993 | Philippon et al. | 424/494 |
| 5,246,714 | A | 9/1993 | Dahlinder et al. | 424/497 |
| 5,783,215 | A | 7/1998 | Arwidsson et al. | 424/501 |
| 5,824,341 | A | 10/1998 | Seth et al. | 424/473 |
| 6,911,217 | B1 | 6/2005 | Gren et al. | 424/497 |
| 8,110,226 | B2 | 2/2012 | Li | 424/490 |
| 2007/0248670 | A1 | 10/2007 | van den Heuvel | 424/471 |
| 2009/0022797 | A1 | 1/2009 | Rossi et al. | 424/471 |
| 2009/0130210 | A1 | 5/2009 | Raheja et al. | 424/479 |

FOREIGN PATENT DOCUMENTS

| CA | 2 425 594 | 5/2002 | ............... A61K 9/50 |
| CA | 2 718 753 | 9/2010 | ............... A61K 9/16 |
| EP | 1 128 819 | 8/2003 | ............... A61K 9/16 |
| WO | WO 01/34139 | 5/2001 | .......... A61K 31/135 |
| WO | WO 2004/105735 | 12/2004 | ............... A61K 9/62 |
| WO | WO 2007/029087 | 3/2007 | ............... A61K 9/50 |
| WO | WO 2012/101653 | 8/2012 | ............... A61K 9/16 |

*Primary Examiner* — Abigail Fisher
*Assistant Examiner* — Daniel L Branson

(57) ABSTRACT

The invention relates to pharmaceutical compositions comprising multilayered multiple units and processes for the preparation thereof.

9 Claims, No Drawings

MULTI-LAYERED, MULTIPLE UNIT PHARMACEUTICAL COMPOSITIONS

FIELD OF THE INVENTION

The present invention relates to pharmaceutical compositions comprising multilayered multiple units and processes for the preparation thereof.

BACKGROUND OF THE INVENTION

Oral controlled-release formulations provide maximum patient compliance and reduce the frequency of dosing to attain effective therapy. The intention of controlled-release formulations is to provide an extended duration of the pharmacological response after administration of the dosage form, than is ordinarily experienced after the administration of an immediate-release dosage form. The purpose of these formulations is to provide a constant concentration of the active substance in body fluids for a certain time period. However, the demand on controlled-release dosage forms is immense, the maximal therapeutic effect is to be reached using a minimum amount of active substance with reduced frequency of dosing and lesser degree of side effects, as well as minimized inter and intra individual effect variations. The dosage form could be single unit or multiple unit dosage form.

Single unit controlled-release dosage forms either pass undisintegrated through the gastrointestinal tract or release the entire drug in a burst (dose dumping). Such dosage forms are dependent upon gastric emptying rates and transit times and are also associated with a lot of intra and inter-individual variations.

Multiple unit dosage forms comprise a multiplicity of individual units contained within a rapid dissolving capsule, or compressed into a tablet, and soon after ingestion upon its dissolution are available as individual units in the G.I.T.

Several advantages with multiple unit dosage forms comprising a large number of small units have been described in the literature. It is, for example, possible to obtain a reproducible emptying of the units from the stomach into the small intestine when the particles are less than 1 to 2 mm. Dispersion over a large area in the gastrointestinal tract can give a more reproducible time for the passage, which is of advantage for the absorption process. In addition, a multiple unit preparation is preferable to one single drug unit as the dose is spread out in the intestine. The risk of local irritation and accumulation of several doses due to constriction in the alimentary canal are also considered to be lower.

U.S. Pat. Nos. 4,927,640 and 5,246,714 describe controlled-release insoluble beads coated with a membrane controlling drug release. Examples of insoluble inert material used are silicon dioxide, glass, or plastic resin particles. The core material has a standardized size and shape, preferably, spherical with an even surface with size of 0.15 to 0.25 mm. The preparation has several advantages, e.g., the particles contain a high percentage of the active ingredient and are not contaminated by soluble inert compounds, which is the case when cores of, e.g., lactose or sugar are covered by a therapeutically active compound. By using small dense particles of, e.g., silicon dioxide as the core material, it is possible to obtain highly concentrated beads (granules) of the active compound which is an advantage for high dosage preparations, e.g., magnesium chloride.

Dosage forms containing multiple layers have several advantages over the prior discussed arts. For example, U.S. Pat. No. 5,783,215 describes the multiple unit dose preparation capable of withstanding the mechanical stress, i.e., during compaction. This has been done by using inert and non-soluble cores of glass or sand particles or soluble cores such as sugar spheres capable of withstanding mechanical stress, in combination with a plasticizing layer. The active substance is dispersed in a solution of the hydrophilic polymer and applied to the core, which is again covered with controlled-release membrane. These beads have excellent mechanical and release characteristics.

WO 2004/105735 by Ranbaxy refers to a controlled-release composition containing units, wherein each unit includes a core, a first layer, and a second layer. In this application it has been disclosed that that inert core (soluble or swellable or insoluble) is first layered with active and one or more hydrophilic polymers. Further, it is layered with second layer of one or more polymers that are effective for controlled-release of active.

U.S. Pat. No. 5,229,135 discloses a sustained-release diltiazem pellet formulation having:
a. a central inactive sphere;
b. a plurality of alternating first and second layers surrounding the sphere to form a core, the first layer comprising a water soluble pharmaceutically acceptable polymeric material and the second layer comprising diltiazem or a pharmaceutically acceptable salt thereof; and
c. an outer coating comprising first inner membrane layers applied to said core, said first inner membrane layers comprising a first water-insoluble pharmaceutically acceptable polymer, and a single outer membrane forming a relatively thick and homogeneous layer surrounding said first inner membrane layers and comprising a second water-insoluble pharmaceutically acceptable polymeric material different from said first water-insoluble pharmaceutically acceptable polymer.

Applying a polymer layer over the inert core before the active layer has some advantages. For example, the amount of time that the solution within the bead would be saturated with respect to drug may be maximized. Thus, by preventing the soluble core from being a reservoir for drug dissolution, the relative time that a saturated solution would remain within the bead during the release period can be increased considerably. This means that a substantially longer zero order drug-release phase (the phase when the drug release rate is essentially constant) will be obtained (and less in the undesirable declining release rate phase). By varying the thickness of the first polymeric layer, drug release profile can be altered in a predictable fashion, in particular for drugs with a moderate to high water-solubility.

A similar kind of dosage form is disclosed in U.S. Pat. No. 6,911,217. It describes a bead comprising (a) a core unit of a substantially water-soluble or water-swellable inert material, (b) a first layer on the core unit of a substantially water-insoluble polymer, (c) a second layer covering the first layer and containing an active ingredient, and (d) a third layer of polymer on the second layer effective for controlled-release of the active ingredient. The first layer of water-insoluble polymer is meant to control water penetration into the core.

U.S. Pat. No. 6,911,217 employs aqueous dispersion of water-insoluble polymers in its first and third layers. Use of polymers based on aqueous dispersion may lead to coalescence. Upon spraying the aqueous polymeric dispersion, the polymer particles are deposited on the surfaces of the pellets as colloidal particles. The colloidal particles come into direct contact with each other and form close-packed arrays due to water evaporation and increase the interfacial tension between water and polymer. Capillary forces then drive the particles to coalesce together. This coalescence may lead to enhance unwanted drug release variability, which should be avoided. Further, the aqueous based system requires high heat of vaporization that might require lengthy processing times leading to economic disadvantages. In addition to this, multiple units coated with aqueous based polymeric system can easily agglomerate in the coating process due to low inertia and momentum.

Therefore, it would be desirable to have a controlled-release composition in the form of multilayered multiple units that will deliver a constant and controlled-release of water-soluble drugs. Further, it is desired to have an advantageous process that would be less time consuming and economical.

SUMMARY OF THE INVENTION

In one aspect, the present invention relates to a multilayered multiple unit composition comprising:
  a. an inert core;
  b. a first layer on the inert core, comprising:
    at least one hydrophilic polymer or hydrophilic substance; and
    at least one hydrophobic polymer or hydrophobic substance;
  c. a second layer onto the first layer, comprising at least one active ingredient;
  d. a third layer onto the second layer, comprising one or more pharmaceutically acceptable polymers effective for controlling or modifying the release of active ingredient; and
  e. optionally, a fourth layer onto the third layer comprising one or more pharmaceutically acceptable polymers;
wherein the first layer is applied as a solution or dispersion or suspension in a non-aqueous based solvent system.

Embodiments of the composition may include one or more of the following features. For example, a seal layer comprising one or more pharmaceutically acceptable polymers may optionally be applied between the second active layer and the third controlled-release or modified-release layer.

In one embodiment, the hydrophilic polymer or hydrophilic substance present in the first layer amounts to 0.1 to 20% of the total weight of the composition. Particularly, the amount is 0.1 to 10% and more particularly the amount is 0.1 to 5%.

In another embodiment, the ratio of hydrophilic polymer or hydrophilic substance to hydrophobic polymer or hydrophobic substance in the first layer may be from about 5:95 to 95:5 by weight.

In yet another embodiment, the active ingredient may include, but are not limited to, antiulcers, analgesics, antihypertensives, antibiotics, antipsychotics, anticancer agents, antimuscarinics, diuretics, antimigraines, antivirals, anti-inflammatory agents, sedatives, antidiabetics, antidepressants, antihistaminics, antiparasitics, antiepileptics and lipid lowering drugs. Particularly, the active ingredient is antimuscarinic and more particularly, the antimuscarinic is tolterodine and its acceptable salts.

In another aspect the present invention relates to a process for preparing a multilayered multiple unit composition comprising the steps of:
  a. providing a inert core;
  b. applying a first layer on the inert core, comprising:
    at least one hydrophilic polymer or hydrophilic substance; and
    at least one hydrophobic polymer or hydrophobic substance;
  c. applying a second layer onto the first layer, comprising at least one active ingredient;
  d. applying a third layer onto the second layer, comprising one or more pharmaceutically acceptable polymers effective for controlling or modifying the release of active ingredient; and
  e. optionally applying a fourth layer onto the third layer comprising one or more pharmaceutically acceptable polymers;
wherein the first layer is applied as a solution or dispersion or suspension in a non-aqueous based solvent system.

In yet another aspect, the present invention relates to a process for preparing a multilayered multiple unit composition comprising the steps of:
  a. providing a inert core;
  b. applying a first layer on the inert core, comprising:
    at least one hydrophilic polymer or hydrophilic substance; and
    at least one hydrophobic polymer or hydrophobic substance;
  c. applying a second layer onto the first layer, comprising at least one active ingredient;
  d. applying a seal layer onto the second layer, comprising one or more pharmaceutically acceptable polymers;
  e. applying a third layer onto the seal layer, comprising one or more pharmaceutically acceptable polymers effective for controlling or modifying the release of active ingredient; and
  f. optionally applying a fourth layer onto the third layer, comprising one or more pharmaceutically acceptable polymers;
wherein the first layer is applied as a solution or dispersion or suspension in a non-aqueous based solvent system.

In one embodiment the seal layer onto the second layer may optionally further include one or more organic acids as stabilizers to prevent any inter-reactions between the drug and the release-controlling or modifying layer.

Embodiments of the composition may include one or more pharmaceutically acceptable excipients, which act in one or more capacities as diluents, binders, plasticizers, lubricants, glidants, colorants or flavoring agents.

The details of one or more embodiments of the inventions are set forth in the description below. Other features and objects of the invention will be apparent from the description and examples.

DETAILED DESCRIPTION OF THE INVENTION

Formulating a controlled-release pharmaceutical composition for water-soluble drugs, that too in the form of multiple units is not so easy. In this invention, the inventors have developed a multilayered multiple-unit composition, that is robust and stable, to deliver the active ingredient in a controlled manner.

The invention relates to a multilayered multiple unit controlled-release composition comprising:
  a. an inert core;
  b. a first layer on the inert core, comprising:
    at least one hydrophilic polymer or hydrophilic substance; and
    at least one hydrophobic polymer or hydrophobic substance;
  c. a second layer onto the first layer, comprising at least one active ingredient;

d. a third layer onto the second layer, comprising one or more pharmaceutically acceptable polymers effective for controlling or modifying the release of active ingredient;

e. a seal layer between the second and third layer, comprising one or more pharmaceutically acceptable polymers; and f. optionally, a fourth layer onto the third layer comprising one or more pharmaceutically acceptable polymers;

wherein the first layer is applied as a solution or dispersion or suspension in a non-aqueous based solvent system.

The term "multiple unit composition" indicates a pharmaceutical composition that includes one or more individual coated units contained in the formulation in such a form that the individual units will be available from the formulation upon disintegration of the formulation in the stomach. The multiple unit pharmaceutical composition or formulation may be a capsule or a tablet that disintegrates in the stomach to give individual units. The multiple units may be formulated as granules, pellets or beads.

The inert core of the composition may include one or more of an inert insoluble, swellable or soluble core. The insoluble or swellable inert core may include one or more of dicalcium phosphate, microcrystalline cellulose or any of the marketed inert cores, for example glass beads, silicate beads, sugar spheres, non-pareils and celphere. The soluble core may include one or more of glucose, mannitol, lactose, xylitol, dextrose, and sucrose.

The first layer of the composition comprises (a) at least one hydrophilic polymer or hydrophilic substance and (b) at least one hydrophobic polymer or hydrophobic substance.

Suitable examples of hydrophilic polymer or hydrophilic substance include, but are not limited to cellulose derivatives such as hydroxypropylcellulose, hydroxypropylmethylcellulose, hydroxyethylcellulose, hydroxymethylcellulose, carboxymethylcellulose, methylcellulose, sodium carboxy methylcellulose or combinations thereof; polyvinylpyrrolidone, polyvinyl acetate, copolymer of vinylpyrrolidone and vinyl acetate, polysaccharides, starch and derivatives, gums, alginates, acrylic acid derivatives, polyethylene glycol, polyalkylene glycols, polyvinyl alcohol, mannitol, sucrose, lactose, xylitol, water-soluble salts of inorganic acids, water-soluble salts of organic acids, non ionic organic compounds having high water-solubility, water-soluble amino acids, gelatin, urea and urea derivatives; or mixtures thereof.

Suitable examples of hydrophobic polymer or hydrophobic substance include, but are not limited to, ethyl cellulose, cellulose acetate, cellulose acetate butyrate, hydroxypropyl methylcellulose phthalate, poly(alkyl) methacrylate, and copolymers of acrylic or methacrylic acid esters, waxes, shellac, hydrogenated vegetable oils; or mixtures thereof.

The second layer of the composition comprise at least one water-soluble active ingredient selected from the group including, but not limited to, antiulcers, analgesics, antihypertensives, antibiotics, antipsychotics, anticancer agents, antimuscarinics, diuretics, antimigraines, antivirals, anti-inflammatory agents, sedatives, antidiabetics, antidepressants, antihistaminics, antiparasitics, antiepileptics and lipid lowering drugs. The active ingredients are water-soluble or water-insoluble. Particularly, the active ingredient is water-soluble.

Suitable examples of water-soluble active ingredient include, but are not limited to, tolterodine tartrate, diltiazem hydrochloride, verapamil hydrochloride, bupropion hydrochloride, metformin hydrochloride, propranolol hydrochloride, dextromethorphan hydrobromide, diphenhydramine hydrochloride, disopyramide hydrochloride, tramadol, fluoxetine hydrochloride, paroxetine hydrochloride, pentoxifylline hydrochloride and the like.

The second layer may additionally comprise a hydrophilic polymer along with the active ingredient that gives plasticity properties to the units and acts as a binder.

Suitable hydrophilic polymers may include, but are not limited to, pharmaceutically acceptable materials like starch, gums, alginates, polysaccharides, polyvinylprrolidone, polyethylene glycol, acrylic acid derivatives, and cellulose derivatives like hydroxypropyl cellulose, hydroxypropyl methylcellulose, hydroxyethylcellulose, hydroxymethylcellulose, carboxymethylcellulose, methylcellulose, sodium carboxy methylcellulose, and mixtures thereof.

The third layer of the composition comprises one or more polymers effective for controlling or modifying the release active ingredient.

The release-controlling polymers may be selected from the group comprising hydrophilic polymers, hydrophobic polymers, or combinations thereof.

Suitable examples of hydrophilic release-controlling polymers include, but are not limited to cellulose derivatives such as hydroxypropylcellulose, hydroxypropylmethylcellulose, hydroxyethylcellulose, hydroxymethylcellulose, carboxymethylcellulose, methylcellulose, sodium carboxy methylcellulose or combinations thereof; polyvinylpyrrolidone, polyvinyl acetate, copolymer of vinylpyrrolidone and vinyl acetate, polysaccharides, polyalkylene glycols, starch and derivatives; or mixtures thereof.

Suitable examples of hydrophobic release controlling polymers include, but are not limited to ethyl cellulose, cellulose acetate, cellulose acetate butyrate, hydroxypropyl methylcellulose phthalate, poly(alkyl)methacrylate, and copolymers of acrylic or methacrylic acid esters, waxes, shellac and hydrogenated vegetable oils. The hydrophobic release controlling polymers may be water-based dispersions of ethyl cellulose and is commercially available as Surelease® or AquaCoat®.

The release modifying polymers may be the enteric polymers and may be selected from any such pharmaceutically acceptable enteric polymers, which would facilitate erosion and breakdown of the pellets in the pH of the lower GI tract. These enteric polymers may be selected from the group consisting of cellulose acetate phthalate, hydroxypropylmethylcellulose phthalate, and additional cellulose ether phthalates, any or the acrylic acid derivates phthalates (available commercially as Eudragits), shellac, zein, or mixtures thereof.

The third layer of release-controlling or modifying layer may also include one or more release regulators. The release regulators may include, but are not limited to, hydroxypropyl methylcellulose, hydroxyethyl cellulose, hydroxypropyl cellulose, methylcellulose, carboxymethylcellulose, polyethylene glycol, polyvinylpyrrolidone, polyvinyl alcohol, polymers with pH-dependent solubility, such as cellulose acetate phthalate or ammonio-methacrylate copolymer and methacrylic acid copolymer; or mixtures thereof.

The seal layer between the second and third layers of the composition comprises one or more pharmaceutically acceptable polymers that include, but are not limited to, ethyl cellulose, hydroxypropyl methylcellulose, hydroxypropyl cellulose, methyl cellulose, carboxymethylcellulose, hydroxymethylcellulose, hydroxyethylcellulose, hydroxypropyl methyl phthalate, cellulose acetate, cellulose acetate trimelliatate, cellulose acetate phthalate; Waxes such as polyethylene glycol; methacrylic acid polymers such as Eudragit® E, L, S, FS, NE, RL and RS; or mixtures thereof.

Alternatively, commercially available coating compositions comprising film-forming polymers marketed under various trade names, such as Opadry® may also be used for coating.

The seal layer may further include one or more organic acids as stabilizers to prevent any inter-reactions between the drug and the release-controlling or modifying layer.

Suitable examples of organic acids used as stabilizers include, but are not limited to tartaric acid, lactic acid, salicylic acid, citric acid, acetic acid, gluconic acid, succinic acid, and oxalic acid. Particularly the organic acid is tartaric acid.

The optional fourth layer, onto the third layer of the composition comprises one or more pharmaceutically acceptable polymers. The polymers may comprise one or more film forming agents and/or pharmaceutically acceptable excipients.

Examples of film forming agents include, but are not limited to ethyl cellulose, hydroxypropyl methylcellulose, hydroxypropyl cellulose, methyl cellulose, carboxymethylcellulose, hydroxymethylcellulose, hydroxyethylcellulose, hydroxypropyl methyl phthalate, cellulose acetate, cellulose acetate trimelliatate, cellulose acetate phthalate; waxes such as polyethylene glycol; methacrylic acid polymers such as Eudragit® RL and RS; or mixtures thereof. Alternatively, commercially available coating compositions comprising film-forming polymers marketed under various trade names, such as Opadry® may also be used for coating.

The composition may further include one or more pharmaceutically acceptable excipients act in one or more capacities as fillers, binders, plasticizers, lubricants, glidants, colorants, and flavoring agents.

Suitable examples of fillers include, but are not limited to, corn starch, lactose, white sugar, sucrose, sugar compressible, sugar confectioners, glucose, sorbitol, calcium carbonate, calcium phosphate-dibasic, calcium phosphate-tribasic, calcium sulfate, microcrystalline cellulose, silicified microcrystalline cellulose, cellulose powdered, dextrates, dextrins, dextrose, fructose, kaolin, lactitol, mannitol, sorbitol, starch, starch pregelatinized, sucrose, and mixtures thereof.

Examples of binders include, but are not limited to, methyl cellulose, hydroxypropyl cellulose, hydroxypropyl methylcellulose, polyvinylpyrrolidone, poloxamer, gelatin, gum Arabic, ethyl cellulose, polyvinyl alcohol, pullutan, pregelatinized starch, agar, tragacanth, sodium alginate, propylene glycol, and mixtures thereof.

Examples of plasticizers include, but are not limited to, propylene glycol, triethylene glycol, oleic acid, ethyleneglycol monoleate, triethyl citrate, triacetin, diethyl phthalate, glyceryl monostearate, dibutyl sebacate, acetyl triethylcitrate, castor oil, and mixtures thereof.

Examples of lubricants and glidants include, but are not limited to, colloidal anhydrous silica, stearic acid, magnesium stearate, calcium stearate, talc, hydrogenated castor oil, sucrose esters of fatty acids, microcrystalline wax, yellow beeswax, white beeswax, and mixtures thereof.

The coloring agents of the present invention may be selected from any FDA approved colors for oral use.

The non-aqueous solvents used for the preparation of solution, dispersion, or suspension may include, but are not limited to alcohols, ethyl alcohol, isopropyl alcohol; ketones, acetone, ethylmethylketone; halogenated hydrocarbons, dichloroethane, trichloroethane and mixtures thereof. The non-aqueous solvent based system includes completely non-aqueous solvents (for example, solvent system comprising organic solvents, inorganic solvents or mixture of both). The non-aqueous solvent based system also includes substantially non-aqueous solvent comprising at most 20% by weight of water. The remainder of the solvent (i.e., at least 80% by weight) is non-aqueous.

The coating of the layers may be done using a conventional coating pan, a spray coater, a rotating perforated pan, or an automated system, such as a centrifugal fluidizing (CF) granulator, a fluidized bed process, or any other suitably automated coating equipment.

The coated multiple units are filled into hard gelatin capsules or compressed into tablets that disintegrate in the stomach to make available a multiplicity of individually coated units.

The present invention is illustrated below by reference to the following example. However, one skilled in the art will appreciate that the specific methods and results discussed are merely illustrative of the invention, and not to be construed as limiting the invention.

Example 1

| Ingredients | Percent w/w Example 1 |
|---|---|
| Inert Core | |
| Sugar Spheres | 77.08 |
| First Layer | |
| Ethyl Cellulose | 8.16 |
| Hydroxypropyl Methyl Cellulose | 1.44 |
| Methanol | Q.S |
| Dichloromethane | Q.S |
| Second Layer | |
| Tolterodine Tartrate | 1.89 |
| Hydroxypropyl Methyl Cellulose | 0.71 |
| Purified Water | Q.S |
| Methanol | Q.S |
| Third Layer | |
| Ethyl Cellulose | 8.04 |
| Hydroxypropyl Methyl Cellulose | 2.68 |
| Methanol | Q.S |
| Dichloromethane | Q.S |

Procedure:
1. Ethyl cellulose and hydroxypropyl methyl cellulose were dissolved in the solvent mixture and coated over sugar spheres, to form the first layer.
2. Tolterodine tartrate and hydroxypropyl methyl cellulose were dissolved in methanol and water mixture and sprayed over the cores of step 1, to form the second layer.
3. Ethyl cellulose and hydroxypropyl methyl cellulose were dissolved in the mixture of methanol and dichloromethane and coated over cores of step 2, to form the third layer.
4. The coated beads were dried and filled into capsules.

Example 2

| Ingredients | Percent w/w |
|---|---|
| *Inert Core* | |
| Sugar Spheres | 80.84 |
| *First Layer* | |
| Ethyl Cellulose | 4.85 |
| Hydroxypropyl Methyl Cellulose | 0.81 |
| Methanol | Q.S |
| Dichloromethane | Q.S |
| *Second Layer* | |
| Tolterodine Tartrate | 1.89 |
| Hydroxypropyl Methyl Cellulose | 0.71 |
| Purified Water | Q.S |
| Methanol | Q.S |
| *Third Layer* | |
| Ethyl Cellulose (30% Aqueous Dispersion) | 9.16 |
| Hydroxypropyl Methyl Cellulose | 1.53 |
| Purified Water | Q.S |

Procedure:
1. Ethyl cellulose and hydroxypropyl methyl cellulose were dissolved in the solvent mixture and coated over sugar spheres, to form the first layer.
2. Tolterodine tartrate and hydroxypropyl methyl cellulose were dissolved in methanol and water mixture and sprayed over the cores of step 1, to form the second layer
3. Ethyl cellulose (30% aqueous dispersion) and hydroxypropyl methyl cellulose were dissolved in the purified water and coated over cores of step 2, to form the third layer.
4. The coated beads were dried and filled into capsules.

Example 3

| Ingredients | Percent w/w |
|---|---|
| *Inert Core* | |
| Sugar Spheres | 78.43 |
| *First Layer* | |
| Ethyl Cellulose | 4.71 |
| Methanol | Q.S |
| Dichloromethane | Q.S |
| *Second Layer* | |
| Tolterodine Tartrate | 1.81 |
| Hydroxypropyl Methyl Cellulose | 0.68 |
| Purified Water | Q.S |
| Methanol | Q.S |
| *Seal Layer* | |
| Hpmc | 3.42 |
| Purified Water | Q.S |
| *Third Layer* | |
| Ethyl Cellulose (30% Aqueous Dispersion) | 9.16 |
| Hydroxypropyl Methyl Cellulose | 1.53 |
| Purified Water | Q.S |

Procedure:
1. Ethyl cellulose was dissolved in the solvent mixture and coated over sugar spheres, to form the first layer.
2. Tolterodine tartrate and hydroxypropyl methyl cellulose were dissolved in methanol and water mixture and sprayed over the cores of step 1, to form the second layer.
3. Hydroxypropyl methyl cellulose was dissolved in water and sprayed over the cores of step 2, to form a seal layer.
4. Ethyl cellulose (30% aqueous dispersion) and hydroxypropyl methyl cellulose were dissolved in the solvent and coated over cores of step 3, to form the third layer.
5. The coated beads were dried and filled into capsules.

Examples 4 and 5

| | Percent w/w | |
|---|---|---|
| Ingredients | Example 4 | Example 5 |
| *Inert Core* | | |
| Sugar Spheres | 66.61 | 66.55 |
| *First Layer* | | |
| Ethyl Cellulose | 7.60 | 7.59 |
| Polyvinylpyrrolidone | 0.40 | 0.40 |
| Isopropyl Alcohol | Q.S | Q.S |
| Dichloromethane | Q.S | Q.S |
| *Second Layer* | | |
| Tolterodine Tartrate | 3.31 | 3.31 |
| Hydroxypropyl Methyl Cellulose | 1.24 | 1.24 |
| Purified Water | Q.S | Q.S |
| *Seal Layer* | | |
| Hydroxypropyl Methyl Cellulose | 4.75 | 4.27 |
| Tartaric Acid | — | 0.47 |
| Purified Water | Q.S | Q.S |
| *Third Layer* | | |
| Ethyl Cellulose (30% Aqueous Dispersion) | 11.83 | 11.94 |
| Hydroxypropyl Methyl Cellulose | 1.49 | 1.47 |
| Purified Water | Q.S | Q.S |
| *Fourth Layer* | | |
| Hydroxypropyl Methyl Cellulose | 2.28 | 2.28 |
| Purified Water | Q.S | Q.S |
| *Lubrication* | | |
| Magnesium Stearate | 0.49 | 0.49 |

Procedure:
1. Ethyl cellulose was dissolved in the solvent mixture and coated over sugar spheres, to form the first layer.
2. Tolterodine tartrate and hydroxypropyl methyl cellulose were dissolved in water and sprayed over the cores of step 1, to form the second layer.
3. Hydroxypropyl methyl cellulose and tartaric acid were dissolved in water and sprayed over the cores of step 2, to form a seal layer.
4. Ethyl cellulose (30% aqueous dispersion) and hydroxypropyl methyl cellulose were dissolved in water and coated over cores of step 3, to form the third layer.
5. Hydroxypropyl methyl cellulose was dissolved in water and sprayed over the cores of step 4, to form the fourth layer.
6. The coated beads were dried and filled into capsules.

While several particular forms of the invention have been illustrated and described, it will be apparent that various modifications and combinations of the invention detailed in the text can be made without departing from the spirit and scope of the invention.

We claim:

1. A multilayered multiple unit, controlled release composition comprising:
   a. an inert core;
   b. a first layer on the inert core configured to permit fluid to reach the core without bursting the core, comprising:
      at least one hydrophilic polymer or hydrophilic substance; and
      at least one hydrophobic polymer or hydrophobic substance wherein the ratio of hydrophilic polymer or substance to hydrophobic polymer or substance is about 1:5.67 to about 1:19;
   c. a second layer onto the first layer, comprising tolterodine tartrate;
   d. a third layer onto the second layer, comprising one or more pharmaceutically acceptable polymers effective for controlling or modifying the release of active ingredient; and
   e. optionally, a fourth layer onto the third layer comprising one or more pharmaceutically acceptable polymers;
   wherein the first layer is applied as a solution or dispersion or suspension in a nonaqueous based solvent system.

2. The composition according to claim 1, wherein the hydrophilic polymer or hydrophilic substance present in the first layer comprises from about 0.1% to about 20% of the total weight of the composition.

3. The composition according to claim 1, wherein the polymers for controlling or modifying the release of active ingredient comprise one or more of hydrophilic polymers, hydrophobic polymers, and combinations thereof.

4. The composition according to claim 1, wherein the fourth layer comprises one or more of ethyl cellulose, hydroxypropyl methylcellulose, hydroxypropyl cellulose, methyl cellulose, carboxymethylcellulose, hydroxymethylcellulose, hydroxyethylcellulose, hydroxypropyl methyl phthalate, cellulose acetate, cellulose acetate trimelliatate, cellulose acetate phthalate; waxes such as polyethylene glycol; methacrylic acid polymers; and mixtures thereof.

5. The composition according to claim 1, further comprising one or more pharmaceutically acceptable excipients comprising fillers, binders, plasticizers, lubricants, glidants, colorants and flavoring agents.

6. The composition according to claim 1, wherein the composition further comprises a seal layer between the second and third layer, comprising one or more pharmaceutically acceptable polymers.

7. The composition according to claim 6, wherein the seal layer comprises one or more of ethyl cellulose, hydroxypropyl methylcellulose, hydroxypropyl cellulose, methyl cellulose, carboxymethylcellulose, hydroxymethylcellulose, hydroxyethylcellulose, hydroxypropyl methyl phthalate, cellulose acetate, cellulose acetate trimelliatate, cellulose acetate phthalate; waxes such as polyethylene glycol; methacrylic acid polymers; and mixtures thereof.

8. The composition according to claim 7, wherein the seal layer further comprises one or more organic acids as stabilizers.

9. The composition according to claim 8, wherein the organic acid is selected from the acids comprising tartaric acid, lactic acid, salicylic acid, citric acid, acetic acid, gluconic acid, succinic acid, and oxalic acid.

* * * * *